(12) United States Patent
Uchida et al.

(10) Patent No.: US 7,522,796 B2
(45) Date of Patent: Apr. 21, 2009

(54) CAMERA INTEGRAL WITH OPTICAL FIBER

(75) Inventors: Tamotsu Uchida, Kanagawa (JP); Hideto Kato, Shizuoka (JP)

(73) Assignee: Panasonic Corporation, Osaka (JP)

( * ) Notice: Subject to any disclaimer, the term of this patent is extended or adjusted under 35 U.S.C. 154(b) by 382 days.

(21) Appl. No.: 10/597,216

(22) PCT Filed: Jan. 17, 2005

(86) PCT No.: PCT/JP2005/000481

§ 371 (c)(1), (2), (4) Date: Jul. 17, 2006

(87) PCT Pub. No.: WO2005/074786

PCT Pub. Date: Aug. 18, 2005

(65) Prior Publication Data

US 2008/0253724 A1  Oct. 16, 2008

(30) Foreign Application Priority Data

Feb. 5, 2004 (JP) .............................. 2004-029181

(51) Int. Cl.
G02B 6/06 (2006.01)

(52) U.S. Cl. ....................... 385/116; 385/115; 385/117; 385/118; 385/119; 385/120

(58) Field of Classification Search ......... 385/115–120; 600/342, 109, 116

See application file for complete search history.

(56) References Cited

U.S. PATENT DOCUMENTS

| 3,818,902 | A | * | 6/1974 | Kinoshita et al. ........... 600/109 |
| 4,648,892 | A | * | 3/1987 | Kittrell et al. ................. 65/387 |
| 4,669,467 | A | * | 6/1987 | Willett et al. .................. 606/7 |
| 5,170,775 | A | * | 12/1992 | Tagami .................... 356/241.4 |
| 7,063,663 | B2 | * | 6/2006 | Kazakevich ................. 600/178 |

FOREIGN PATENT DOCUMENTS

| JP | 8-332170 | 12/1996 |
| JP | 2002-136473 | 5/2002 |

\* cited by examiner

*Primary Examiner*—Frank G Font
*Assistant Examiner*—Guy G Anderson
(74) *Attorney, Agent, or Firm*—Pearne & Gordon LLP (57) ABSTRACT

A camera (1) has a tubular housing (3) having an emission window (7). A unitized optical fiber bundle (9) is provided on the inner surface of the housing (3) by utilizing a bundle of light guiding optical fibers on the inner surface. The unitized optical fiber bundle (9) is placed on and bonded to the inner surface of the housing (3) with the fibers bonded together by a bonding agent. An end section of the unitized optical fiber bundle (9) reaches the emission window (7) of the housing (3) to be exposed. The camera (1) has sufficient waterproof capability and is easy to produce, and capable of avoiding a decrease in the amount of light.

4 Claims, 10 Drawing Sheets

CAMERA INTEGRAL WITH OPTICAL FIBER

TECHNICAL FIELD

The present invention relates to a camera integral with optical fibers.

BACKGROUND ART

Conventionally, a camera integral with optical fibers is used, for example, for dental or other medical uses. This kind of camera is required to be small, as well as to light up an area to be treated. In order to meet these requirements, a camera is provided with an illumination device using optical fibers. Such a camera is disclosed, for example, in Japanese laid-open publication No. Hei. 8-332170A (pages 3 to 4, and FIG. 1).

Figure 11:
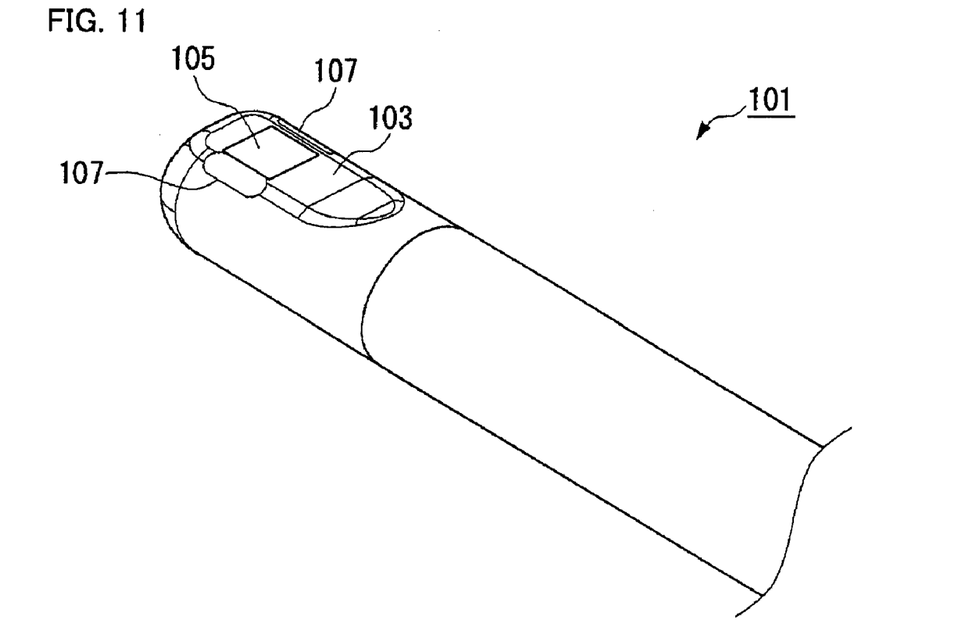
FIG. 11 is a perspective view showing a configuration example of a conventional camera integral with optical fibers.

FIG. 11 shows a front-end part of a conventional camera integral with optical fibers. A camera 101 has a tubular housing 103, in which a CCD or other imaging devices and an image processing circuit are housed. On the side of the front end of the housing 103 is provided a shooting window 105, in which a prism is inserted. Light that enters through the shooting window 105 is bent by the prism and guided in the tube direction. Emission windows 107 are placed as an illumination device on both sides of the shooting window 105.

Figure 12:
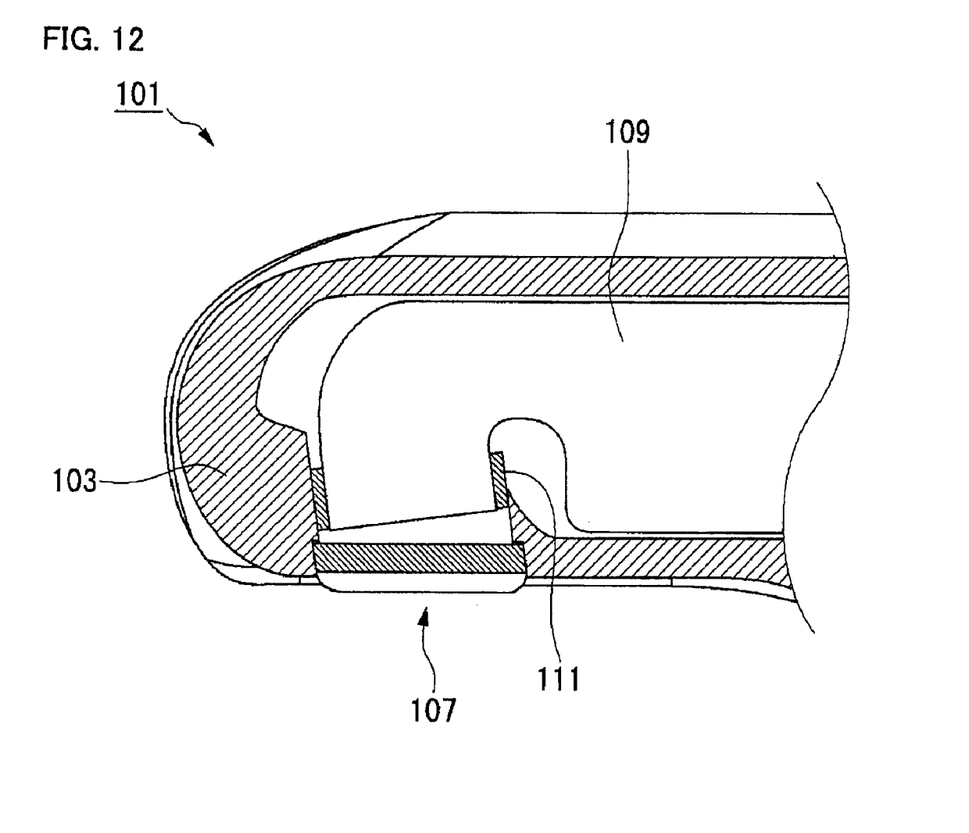
FIG. 12 is a cross-sectional view showing the configuration example of the conventional camera integral with optical fibers.

FIG. 12 is a cross section of the camera of FIG. 11. As shown in the figure, an optical fiber component 109 is fixed in the housing 103. The optical fiber component 109 is an aggregate of thin fibers. Many thin fibers are bundled with a front-end fitting 111 and hardened by a bonding agent, thus producing the part having the configuration shown in the figure. This separate part, the optical fiber component 109, is fixed in the housing 103 by hand.

In the assembling work, the optical fiber component 109 is inserted into the housing 103 from behind so that the front-end fitting 111 goes farther and farther into the housing 103, and then the front-end fitting 111 is placed near the emission window 107. When used, the optical fiber component 109 guides illumination light, which is then emitted from the emission window 107.

Additionally, sapphire glass is inserted in and bonded to the emission window 107, thus ensuring sufficient waterproof capability.

As described above, the optical fiber component, that is a separate component bundled with the front-end fitting, is fixed to the conventional camera integral with optical fibers. For this reason, it is not easy to form the part using the fitting, to incorporate the part, and to incorporate the optical fiber component into the housing. In addition, since the sapphire glass for waterproof use is inserted in the emission window 107 in the conventional camera integral with optical fibers, light emitted from the optical fibers is reflected off the sapphire glass. Consequently, the amount of light decreases by the amount corresponding to the reflection.

DISCLOSURE OF THE INVENTION

Problems to be Solved by the Invention

A purpose of the invention made in the above-mentioned background is to provide a camera integral with optical fibers that has sufficient waterproof capability, is easy to produce, and prevents a decrease in the amount of light.

Means for Solving the Problems

A camera integral with optical fibers of the invention comprises: a tubular housing having an emission window; and a unitized optical fiber bundle which is a bundle of light guiding optical fibers unitized on an inner surface of the housing, wherein the unitized optical fiber bundle is provided on and bonded to the inner surface of the housing with the fibers bonded together by a bonding agent, and wherein an end section of the unitized optical fiber bundle reaches the emission window to be exposed.

There are other aspects of the invention as described below. This disclosure of the invention therefore intends to provide part of aspects of the invention and does not intend to limit the scope of the invention described and claimed herein.

DESCRIPTION OF THE SYMBOLS

1: camera
3: housing
5: shooting window
7: emission window
9: unitized optical fiber bundle
11: inner surface 13: end section
15: exposed section
17: housing surface
19: rear section
21: optical fiber bundle
23: silicone tube
25: insert pipe
27: rear end
29: rear opening
31: inner mold
33: outer mold

BEST MODE OF EMBODYING THE INVENTION

Now, the invention will be described in detail. However, the following detailed description and appended drawings are not intended to limit the invention. Alternatively, the scope of the invention is defined by the appended claims.

A camera integral with optical fibers of this embodiment comprises: a tubular housing having an emission window; and a unitized optical fiber bundle which is a bundle of light guiding optical fibers unitized on an inner surface of the housing, wherein the unitized optical fiber bundle is provided on and bonded to the inner surface of the housing with the fibers bonded together by a bonding agent, and wherein an end section of the unitized optical fiber bundle reaches the emission window to be exposed.

In this configuration, since the above unitized optical fiber bundle, a bundle of optical fibers unitized on the inner surface of the housing, is provided, optical fibers as a separate component bundled with a front-end fitting can be eliminated, and the assembly work of fixing optical fibers becomes unnecessary. Consequently, the production becomes easy. In addition, the end section of the unitized optical fiber bundle exposed directly from the housing allows conventional sapphire glass to be eliminated, while ensuring sufficient waterproof capability. A decrease in the amount of light caused by sapphire glass can therefore be avoided. In this way, a camera integral with optical fibers can be provided that has sufficient waterproof capability, is easy to produce, and prevents a decrease in the amount of light.

In this camera integral with optical fibers, an exposed surface of the unitized optical fiber bundle in the emission window is on the same level with a surrounding housing surface.

In this configuration, a structure can be easily produced in which an end section of the unitized optical fiber bundle is exposed from the housing. The exposed surface of the unitized optical fiber bundle may have a common work surface with the surrounding housing surface.

As described above, the camera integral with optical fibers having the above configuration carries the advantage that it has sufficient waterproof capability, is easy to produce, and can avoid a decrease in the amount of light.

Another aspect of the invention is a method of producing a component of the camera integral with optical fibers. This method will also be described in the embodiment. This method brings the advantage of facilitating the production of the component of the camera integral with optical fibers.

Now, the camera integral with optical fibers of the embodiment of the invention will be described with reference to the drawings.

Figure 1:
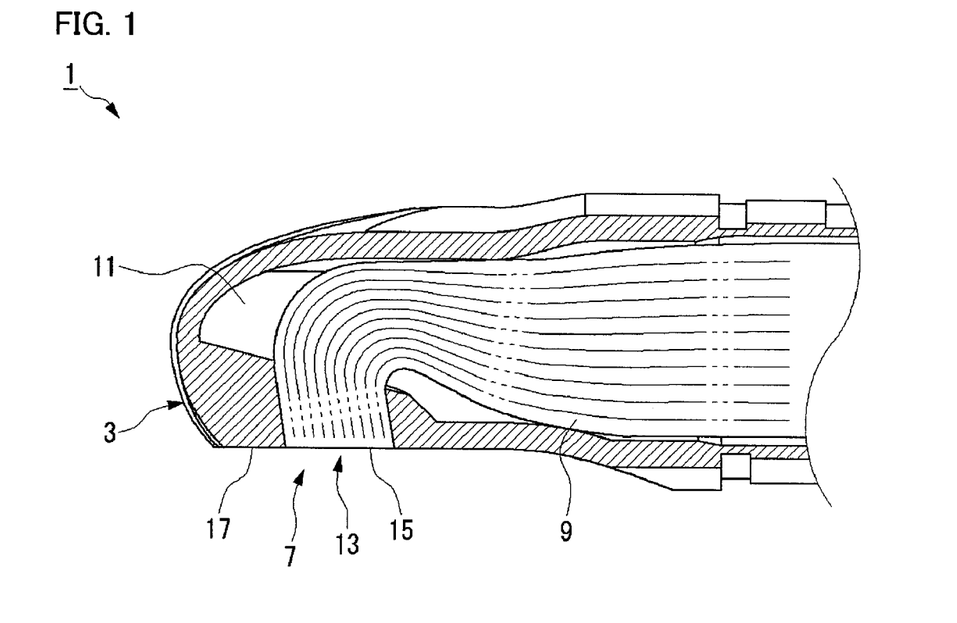
FIG. 1 shows a cross section of a camera integral with optical fibers according to an embodiment of the invention.
Figure 2:
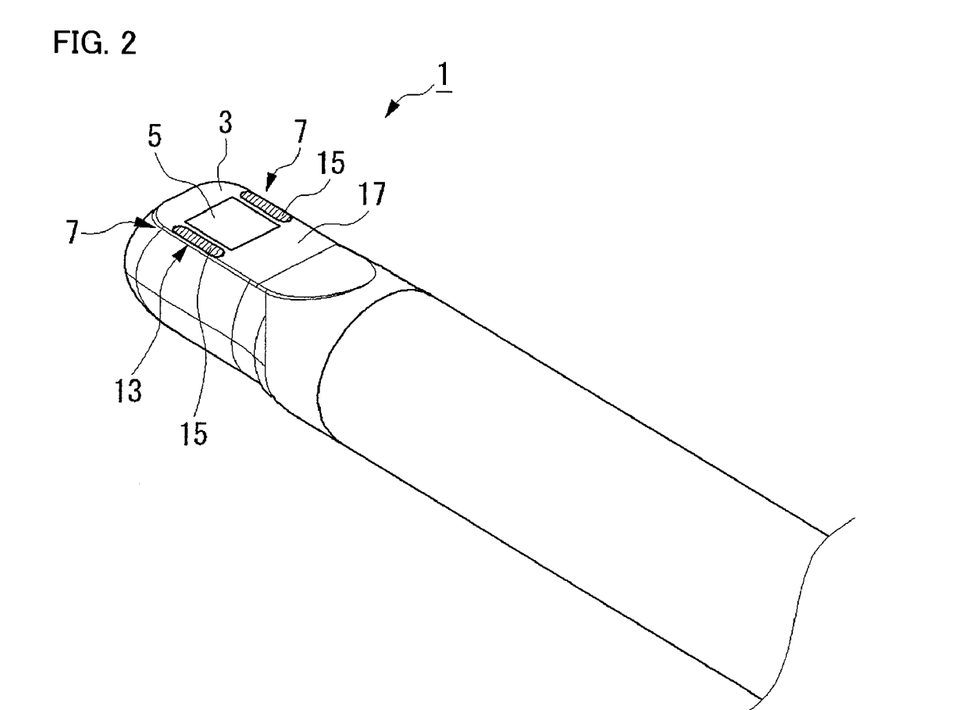
FIG. 2 shows a perspective view of the camera integral with optical fibers according to the embodiment of the invention.

FIG. 1 is a cross-sectional view showing a camera integral with optical fibers of an embodiment of the invention, and FIG. 2 is a perspective view of its external appearance. As shown in FIG. 2, a camera 1 is almost the same in appearance as conventional cameras. The camera 1 has a tubular housing 3, which is a stainless-steel camera case. In the housing 3 are housed a CCD or other imaging device and an image processing circuit. On the side of the front end of the housing 3 is provided a shooting window 5, in which a prism is inserted. Light that enters through the shooting window 5 is bent by the prism and guided in the tube direction (hereinafter meaning the longitudinal direction of the tube), and reaches the imaging device through an optical system. Emission windows 7 are placed as an illumination device on both sides of the shooting window 5.

In the cross section of FIG. 1, the housing 3 incorporates a bundle of optical fibers. In the embodiment, the bundle of optical fibers is unitized on the inner surface of the housing. This bundle of optical fibers is called the "unitized optical fiber bundle." One optical fiber is, for example, 30 micrometers in diameter. The unitized optical fiber bundle 9 therefore comprises a great many optical fibers.

The unitized optical fiber bundle 9 is placed like a membrane on an inner surface 11 of the housing 3. The unitized optical fiber bundle 9 comprises a lot of thin optical fibers, which are bonded to the inner surface 11 with the fibers bonded together by a bonding agent. Though not shown in FIG. 1, the unitized optical fiber bundle 9 is divided into two halves corresponding to the two emission windows 7. Each half covers approximately half of the inner surface 11 of the housing 3.

In the housing 3, the unitized optical fiber bundle 9 is provided in the tube direction, and is bent in the front-end part of the housing 3 toward the emission window 7. Actually, each one of the optical fibers is bent in the bent section. In addition, the cross-sectional shape of the unitized optical fiber bundle 9 changes in the bent section. That is, the cross-sectional shape changes from the membrane-like shape running along the inner surface of the housing 3 to an approximately rectangular shape spreading along the emission window 7.

An end section 13 of the unitized optical fiber bundle 9 reaches the emission window 7 of the housing 3 to be exposed. The end section 13 is full of many optical fibers, and a bonding agent is filled between each of the optical fibers. This configuration ensures sufficient waterproof capability. At the emission window 7, an exposed surface (end surface) of an exposed section 15 of the unitized optical fiber bundle 9 is enclosed by a housing surface 17 surrounding the exposed surface, and the exposed surface (end surface) is a common work surface with the surrounding housing surface 17. Consequently, the exposed surface (end surface) is on the same level with the surrounding housing surface 17.

Figure 3:
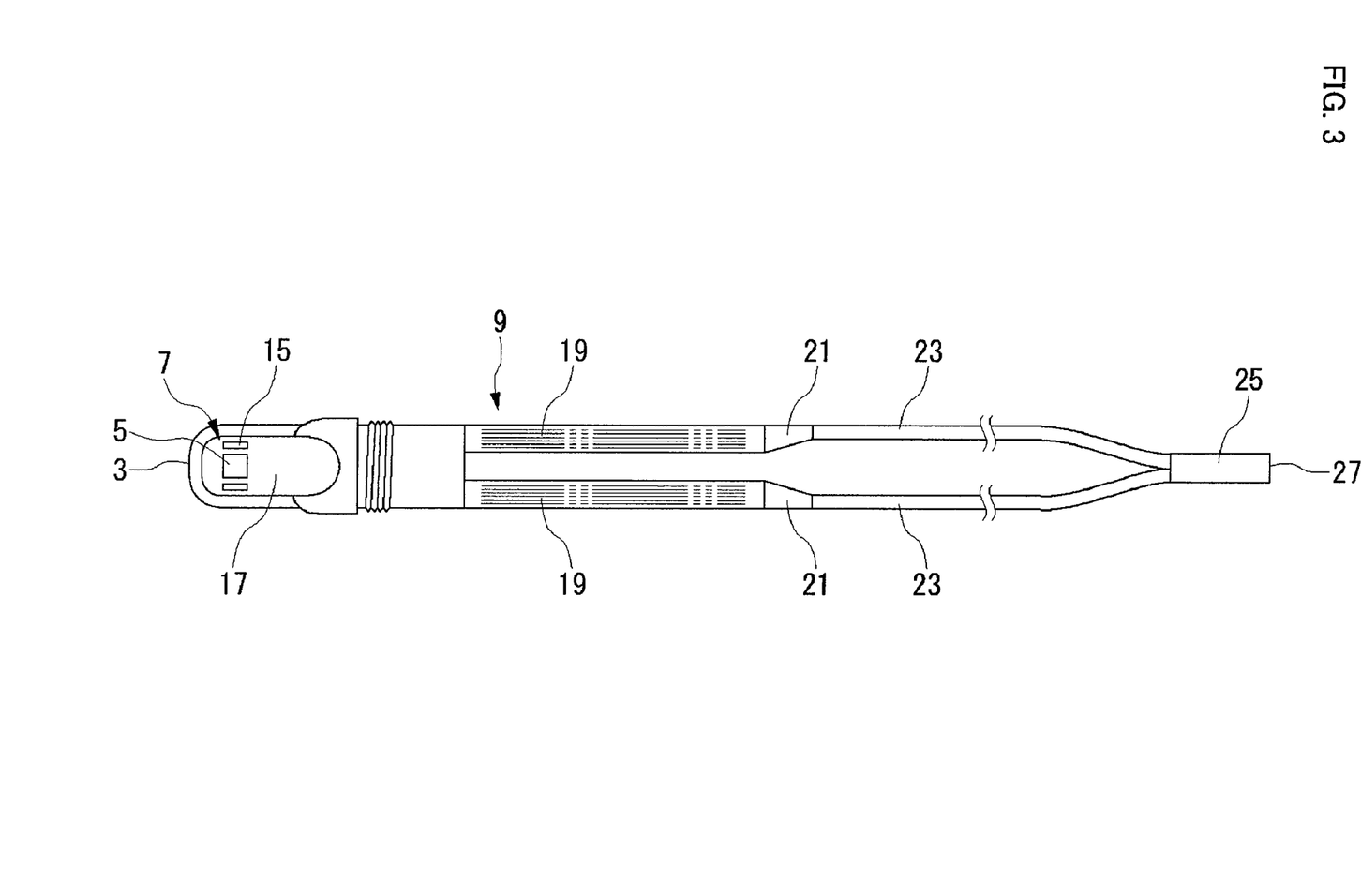
FIG. 3 shows a housing and optical fibers of the camera integral with optical fibers according to the embodiment of the invention.

FIG. 3 shows the housing 3 as one component comprising the unitized optical fiber bundle 9. Rear sections 19 of the unitized optical fiber bundle 9 protrude from the rear of the housing 3. In the following description, the rear means a direction away from the front end along the tube direction of the housing 3.

As previously described, the unitized optical fiber bundle 9 is divided into two halves in the housing 3, and each half covers approximately half of the housing 3. Corresponding to this configuration, the two rear sections 19 are also seen at the rear of the housing 3. As with the fibers in the housing 3, each rear section 19 is molded like a membrane.

In a completed camera, the rear section 19 is housed in another housing, not shown, in the rear. The rear housing is coupled to the housing 3, and is larger in outer diameter than the housing 3. The rear housing also incorporates a substrate and a light source. Additionally, an imaging cable extends from the rear housing.

Rear sections further behind the rear sections 19 of the unitized optical fiber bundle 9 are not-yet bonded optical fiber bundles 21 (The rear section 19 may be called a middle section, and alternatively the rear section behind the rear section 19 may be called a rear section. The rear section behind the rear section 19 may also be called a tail section). The optical fiber bundle 21 is bundled here with a silicone tube 23. The optical fiber bundles 21 are then inserted into an insert pipe 25 in the rear of the silicone tubes 23. The optical fiber bundles 21, divided into two, join together at the insert pipe 25.

On a rear end 27 of the insert pipe 25 is formed a common ground surface of the insert pipe 25 and the optical fiber bundles 21. Though not shown in the figure, light emitted from the light source is guided by another optical fiber and then passed on through the rear end 27 of the insert pipe 25. The light is then guided through the unitized optical fiber bundle 9 to the front end of the camera, and is emitted from the emission window 7. The two-way split structure provided in the light guide system facilitates parts replacement at the time of trouble, and can therefore improve serviceability.

Figure 4:
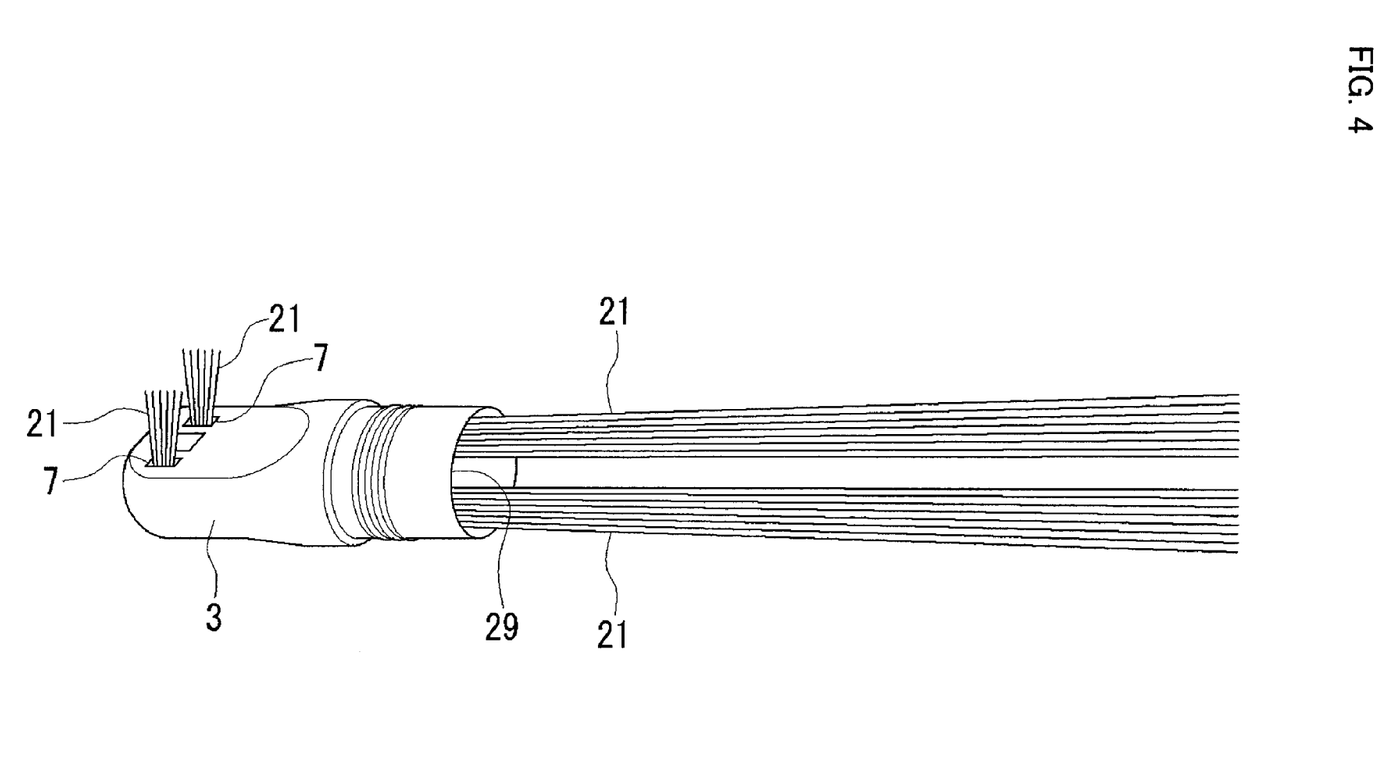
FIG. 4 shows a step of inserting optical fibers in a method of producing the camera integral with optical fibers according to the embodiment of the invention.

A method of producing the camera integral with optical fibers of the embodiment will be described next. As shown in FIG. 4, the not-yet bonded optical fiber bundle 21 is inserted into the housing 3 in the first place. An optical fiber is, for example, approximately 30 micrometers in diameter, so a great many optical fibers are inserted. The optical fiber bundle 21 is inserted from the emission window 7 and comes out from a rear opening 29 of the housing 3. At this time, each fiber of the optical fiber bundle 21 bends in the housing 3. As shown in the figure, the optical fiber bundle 21 thus goes through the housing 3 and protrudes from the emission window 7 and from the rear opening 29.

Figure 5:
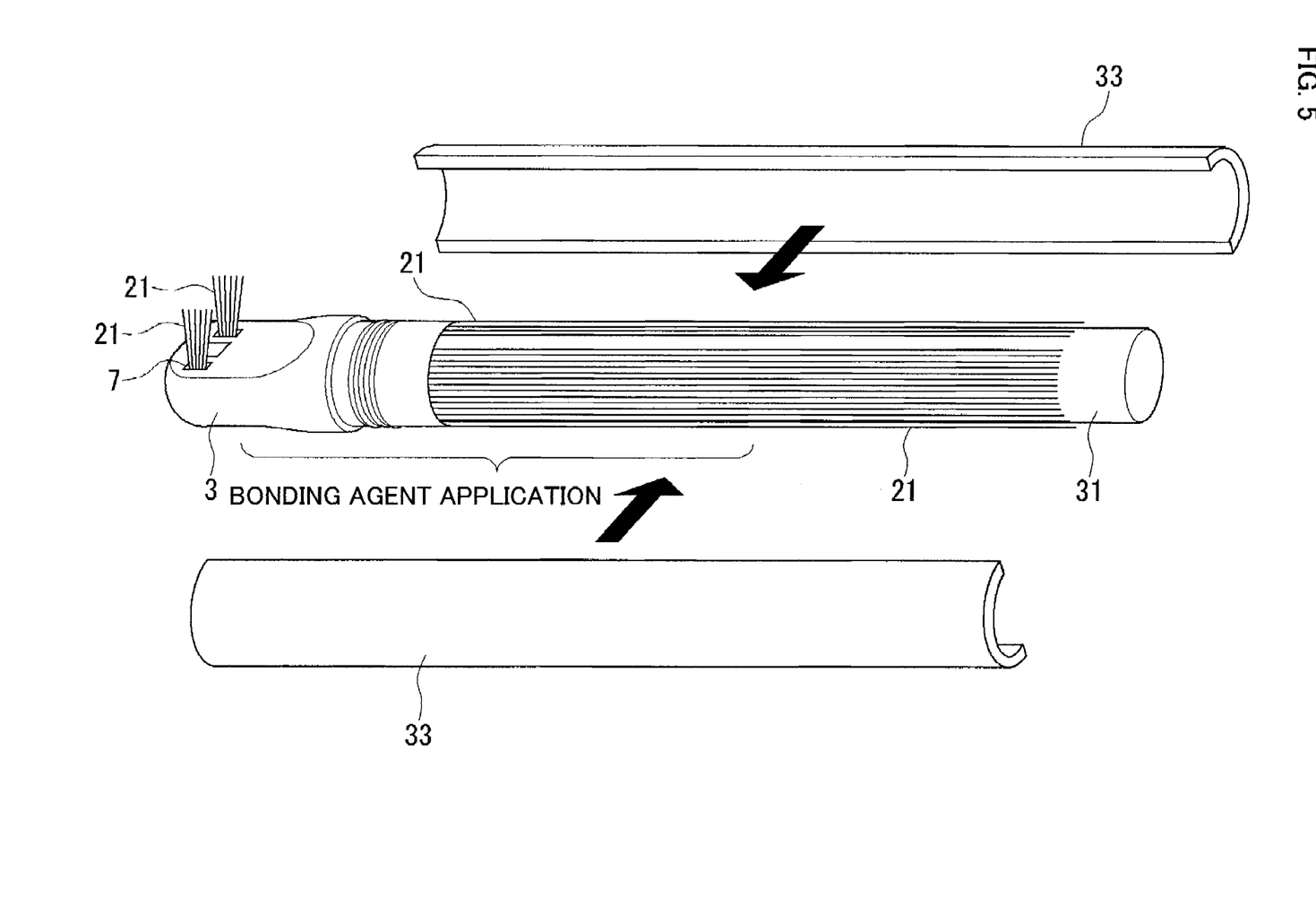
FIG. 5 shows a step of molding a fiber bundle in the method of producing the camera integral with optical fibers according to the embodiment of the invention.

As shown in FIG. 5, a bonding agent is applied to part to be unitized of the optical fiber bundle 21. The application area is an area corresponding to the above-described unitized optical fiber bundle 9. The bonding agent is also applied to an area corresponding to the rear section 19. The bonding agent is, for example, a thermosetting silicone adhesive. FIG. 5 also shows that an inner mold 31 is attached to the housing 3. An outer mold 33 is then attached around the inner mold 31.

The inner mold 31 is a rod-like member that corresponds to a core. The inner mold 31 is inserted into the housing 3. In the state where it is inserted, a gap is formed between the inner surface 11 of the housing 3 and the inner mold 31. The shape of the gap corresponds to the unitized optical fiber bundle 9 to be molded. The optical fiber bundles 21 with the bonding agent applied thereto are put in this gap. In an area where the unitized optical fiber bundle 9 is not formed, the inner mold 31 is shaped so that it is in close contact with the housing 3. This close-contact section locates the inner mold 31 against the housing 3.

The outer mold 33 has a cylindrical shape. The outer mold 33 is attached in a state where the inner mold 31 is inserted into the housing 3. The outer mold 33 is attached around part of the inner mold 31 which protrudes from the housing 3. As shown in the figure, the outer mold 33 has a two-division structure, and the two halves are put together.

The outer mold 33 forms a gap with the inner mold 31. The shape of this gap corresponds to the rear sections 19 of the unitized optical fiber bundle 9. Part of the optical fiber bundle 21 that protrudes toward the rear from the housing 3 is put in this gap. However, the inner mold 31 is in close contact with the outer mold 33 in some upper and lower sections. The optical fiber bundles 21 do not get into these close-contact sections. This also corresponds to the above-described two-division structure of the rear sections 19.

Figure 6:
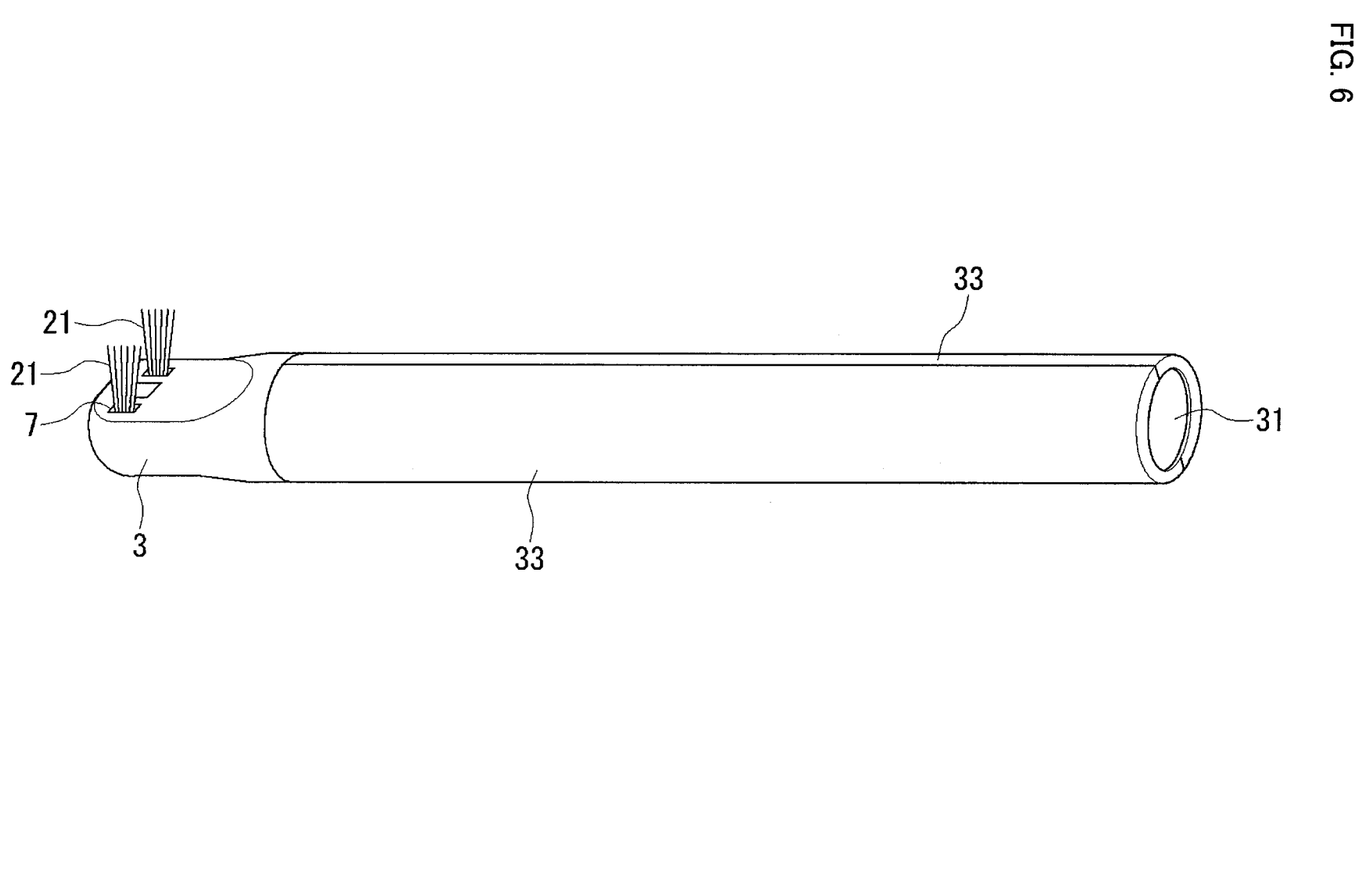
FIG. 6 shows the step of molding the fiber bundle in the method of producing the camera integral with optical fibers according to the embodiment of the invention.
Figure 7:
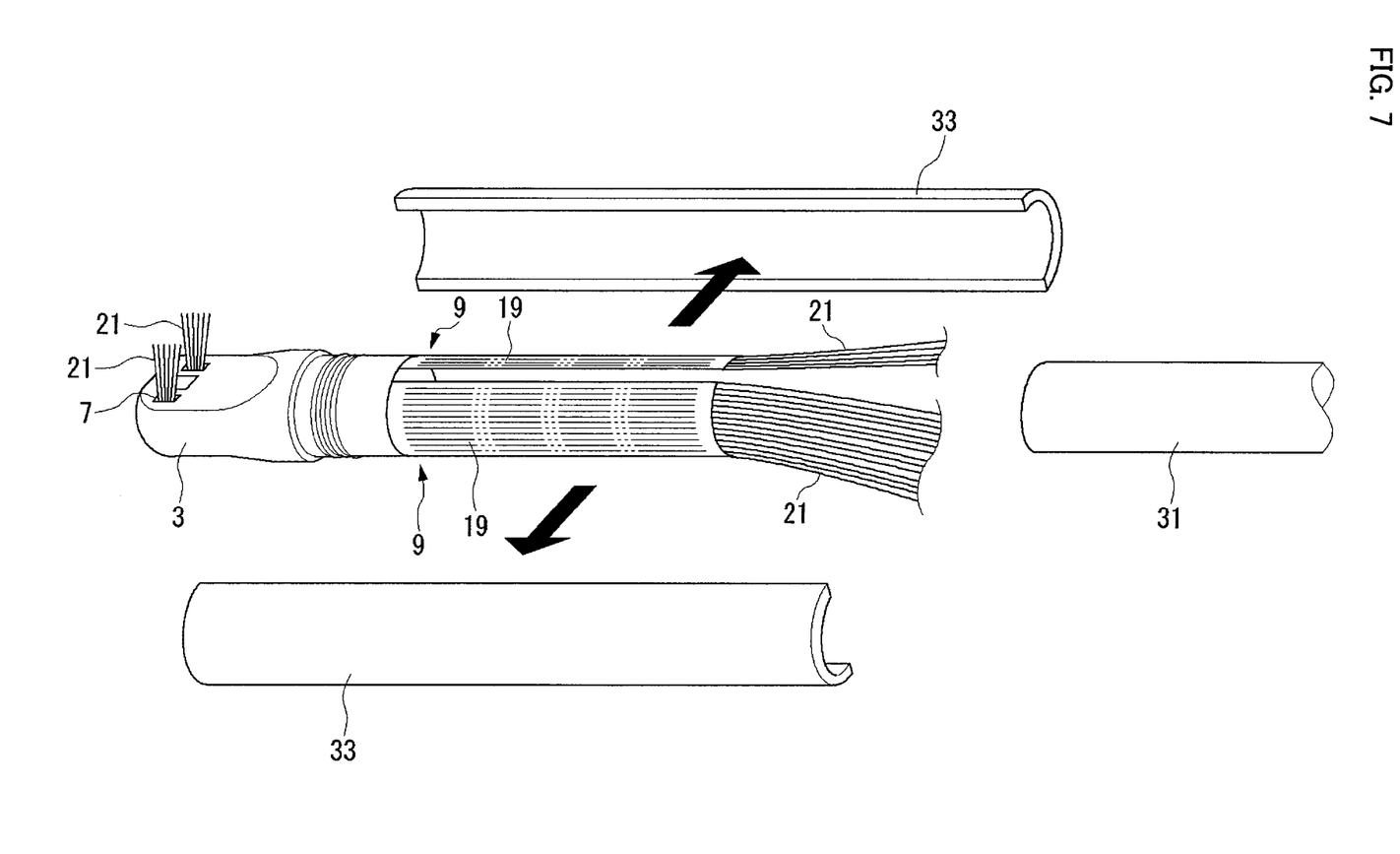
FIG. 7 shows the step of molding the fiber bundle in the method of producing the camera integral with optical fibers according to the embodiment of the invention.

Referring to FIG. 6, the bonding agent is cured in the state where the inner mold 31 and the outer mold 33 are attached. For example, the cure process is performed at a temperature of 80 degrees Celsius for two hours. After the cure, the outer mold 33 and the inner mold 31 are removed as shown in FIG. 7. The optical fiber bundles 21 are bonded like a membrane on the inner surface 11 of the housing 3 and unitized with the housing 3 to be the unitized optical fiber bundle 9. The rear sections 19 of the unitized optical fiber bundle 9 are also molded like a membrane as a result of being put between the inner mold 31 and the outer mold 33. The rear sections 19 protrude from the rear of the housing 3. In the rear further behind the rear sections 19, the optical fibers are still free and separated from each other since the bonding agent was not applied thereto.

Figure 8:
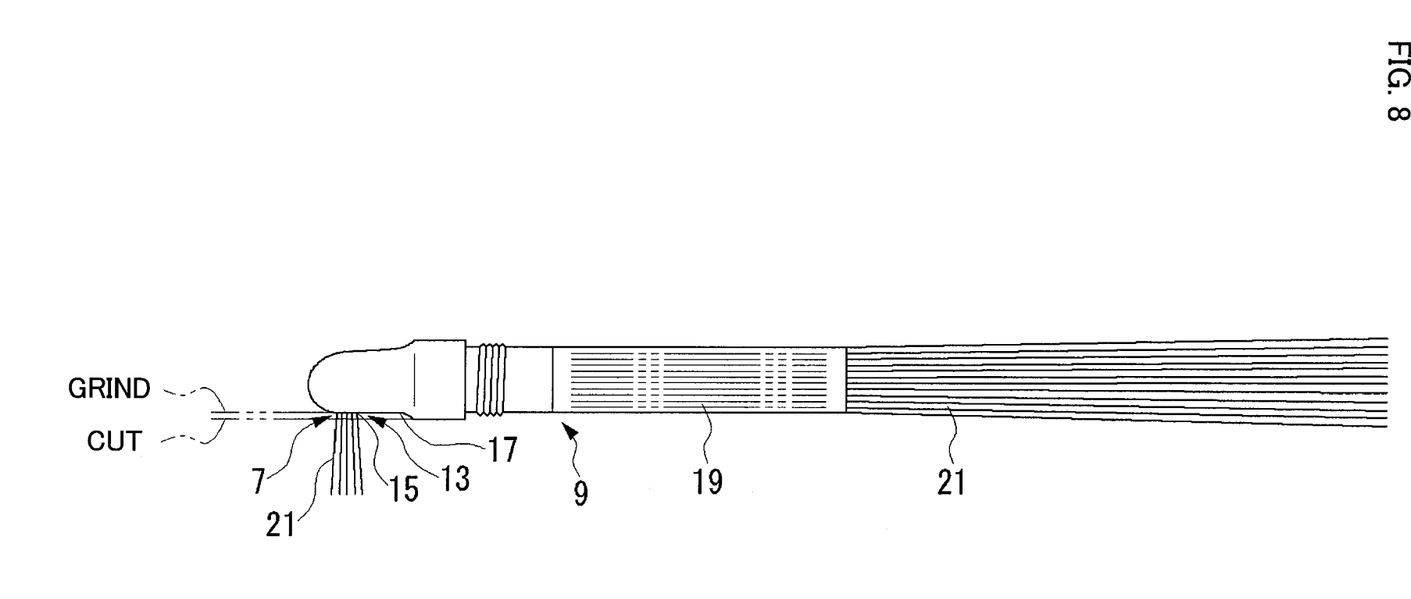
FIG. 8 shows a step of grinding an emission window in the method of producing the camera integral with optical fibers according to the embodiment of the invention.

In the next step, part of the optical fiber bundle 21 that protrudes from the emission window 7 is cut off as shown in FIG. 8. An end section of the optical fiber bundle 21 is first cut leaving approximately 2 mm. This 2 mm section is then cut off by grinding. In the grinding process, the optical fiber bundle 21 is ground together with the housing surface 17 surrounding the emission window 7. As a result, the exposed section 15 of the end section 13 of the unitized optical fiber bundle 9 becomes a surface that is on exactly the same level with the surrounding housing surface 17. The housing 3 is subjected to a blast treatment after the grinding.

Figure 9:
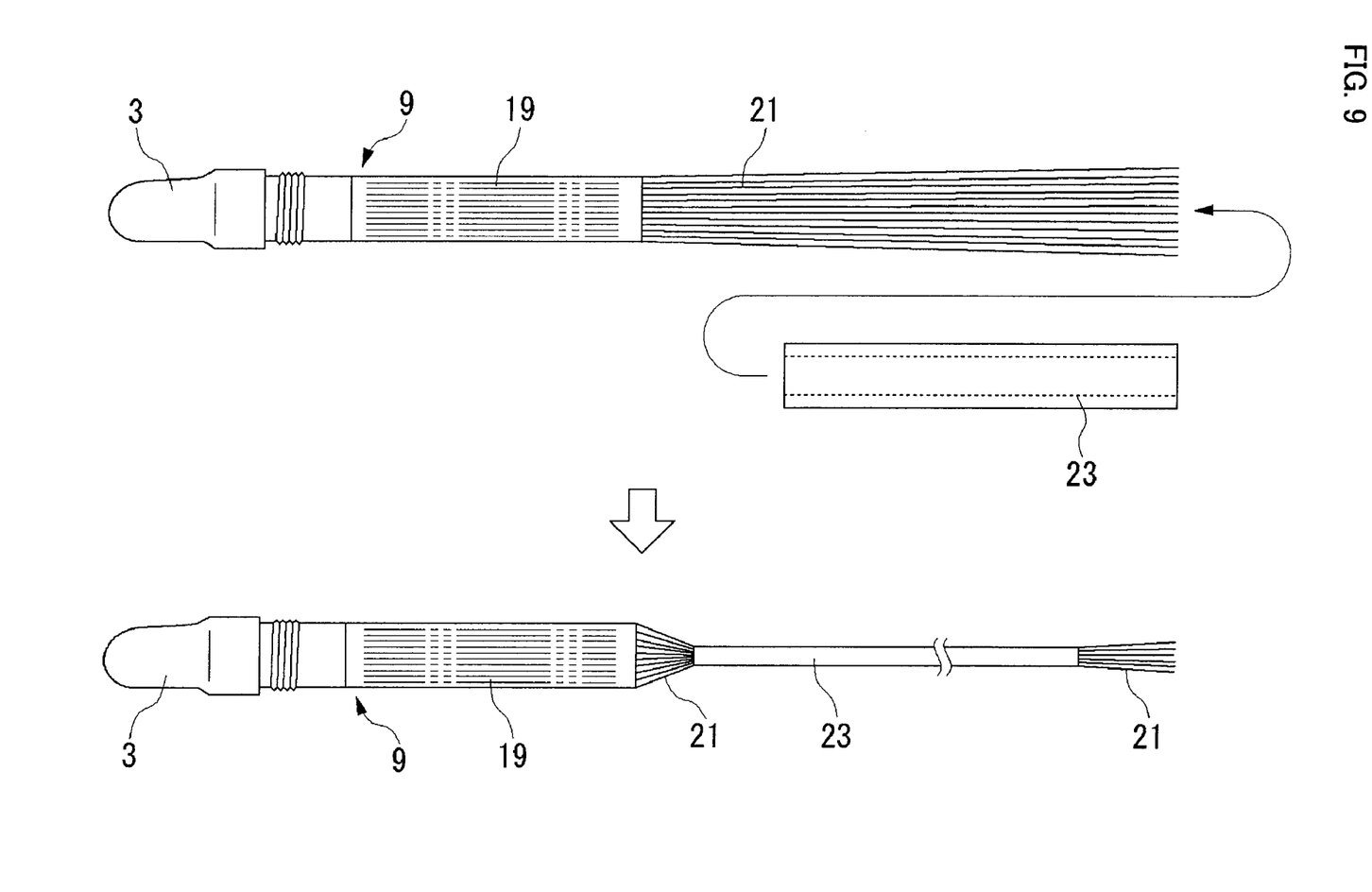
FIG. 9 shows a step of attaching a silicone tube in the method of producing the camera integral with optical fibers according to the embodiment of the invention.
Figure 10:
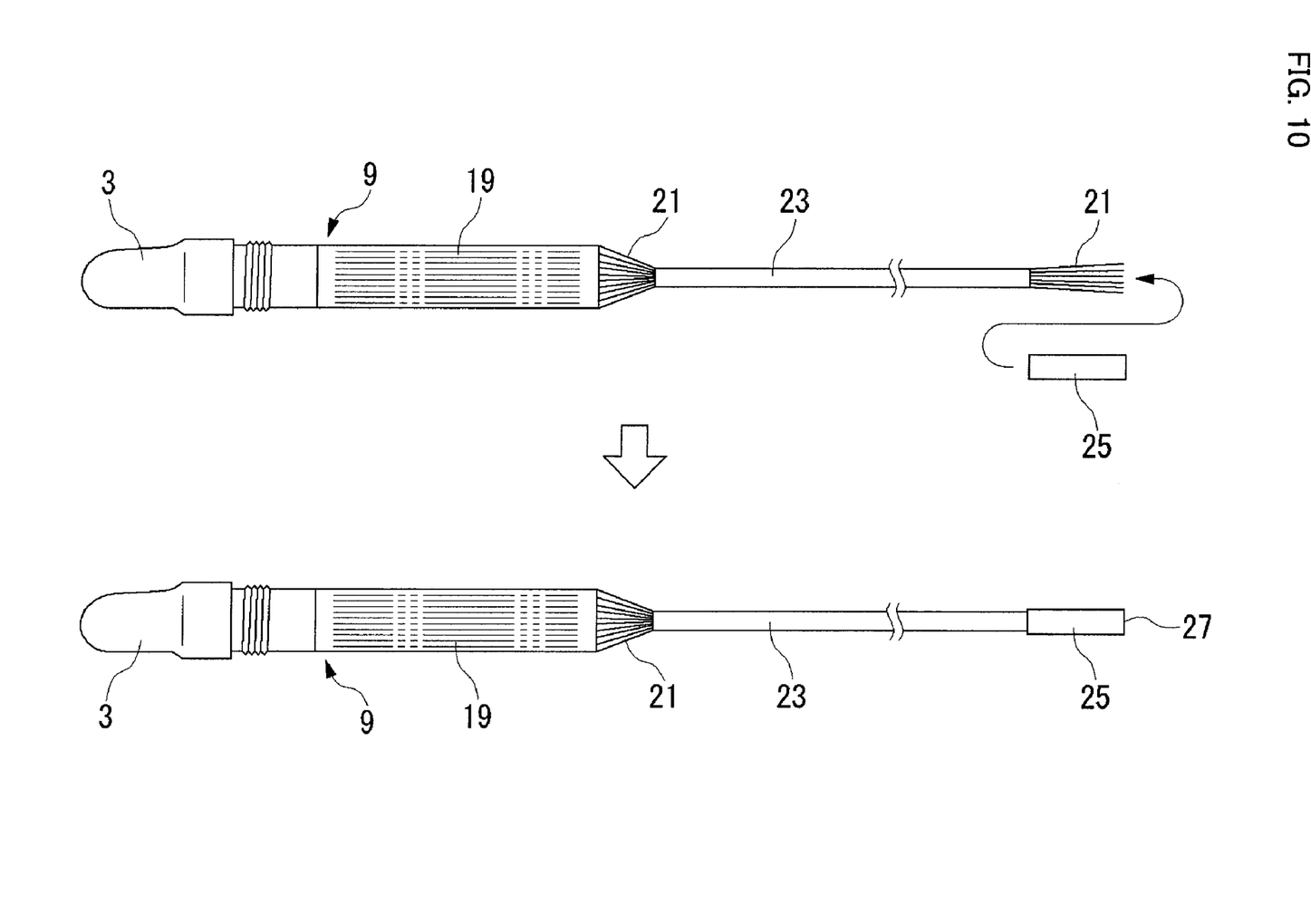
FIG. 10 shows a step of cutting an insert pipe in the method of producing the camera integral with optical fibers according to the embodiment of the invention.

As shown in FIG. 9, part of the optical fiber bundle 21 is left not-yet bonded in the rear sections further behind the rear sections 19 of the unitized optical fiber bundle 9. This part of the optical fiber bundle 21 is drawn through the silicone tube 23 to be bundled. The silicone tube 23 circularly bundles the optical fiber bundle 21 by heat shrinkage. In addition, as shown in FIG. 10, the optical fiber bundle 21 is inserted into and bonded to the insert pipe 25 in the rear of the silicone tube 23. The optical fiber bundles 21, divided into two, join together at this insert pipe 25. The rear end 27 of the insert pipe 25 is then ground together with the optical fiber bundle 21 inside.

In this way, optical fibers are unitized with the housing 3. A prism is inserted into the shooting window 5 of the housing 3. The housing 3 is also coupled with another housing in the rear (see FIG. 2). It further incorporates an imaging device, a substrate, a light source, an imaging cable, and other various components, so that the camera 1 is brought to completion.

As described above, the camera integral with optical fibers 1 of the embodiment is provided with the light-guiding unitized optical fiber bundle 9 unitized on the inner surface of the housing, and therefore optical fibers as a separate component bundled with a front-end fitting can be eliminated. The assembly work of fixing optical fibers becomes unnecessary. Consequently, the production becomes easy. In addition, the end section of the unitized optical fiber bundle 9 is exposed directly from the emission window 7 of the housing 3. As a result, conventional sapphire glass can be eliminated while sufficient waterproof capability is ensured. A decrease in the amount of light caused by sapphire glass can therefore be avoided. In this way, the camera integral with optical fibers 1 can be provided that has sufficient waterproof capability, is easy to produce, and prevents a decrease in the amount of light.

Additionally, in the camera integral with optical fibers 1 of the embodiment, the optical fiber bundle is placed like a membrane on the inner surface of the housing and bonded thereto. The optical fiber not taking up much space also has an advantage in miniaturization, and can contribute to a reduction in the diameter of the camera.

Moreover, in the camera integral with optical fibers 1 of the embodiment, the exposed surface of the unitized optical fiber bundle 9 in the emission window is on the same level with the surrounding housing surface, so that the structure can be easily provided in which the end section of the unitized optical fiber bundle 9 is exposed from the housing. In the above example, the both surfaces are worked at a time.

Furthermore, a method of producing the camera integral with optical fibers and a component thereof has been described in the above embodiment. Another aspect of the invention is such a method of producing the camera integral with optical fibers or a component thereof. In the above example, the inner mold is used and the unitized optical fiber bundle is suitably formed. The above method can eliminate an optical fiber bundle as a separate component bundled with a front-end fitting. The assembly work of fixing optical fibers therefore becomes unnecessary. Consequently, the production becomes easy.

While there has been described what are at present considered to be preferred embodiments of the invention, it will be understood that various modifications may be made thereto, and it is intended that appended claims cover all such modifications as fall within the true spirit and scope of the invention.

INDUSTRIAL APPLICABILITY

The invention has advantages that it ensures sufficient waterproof capability, is easy to produce, and can avoid a decrease in the amount of light, and it is useful as a camera for dentists or the like.

The invention claimed is:

1. A camera integral with optical fibers, said camera comprising: a tubular housing having an emission window; and a unitized optical fiber bundle which is a bundle of light guiding optical fibers unitized on an inner surface of said housing, wherein said unitized optical fiber bundle is provided on and bonded to said inner surface of said housing with said fibers bonded together by a bonding agent, and wherein an end section of said unitized optical fiber bundle reaches said emission window to be exposed.

2. The camera integral with optical fibers according to claim 1, wherein an exposed surface of said unitized optical fiber bundle in said emission window is on the same level with a surrounding surface of said housing.

3. The camera integral with optical fibers according to claim 1, wherein said unitized optical fiber bundle is placed like a membrane on said inner surface of said housing.

4. The camera integral with optical fibers according to claim 1, wherein said unitized optical fiber bundle is divided into two halves corresponding to two emission windows.

\* \* \* \* \*

UNITED STATES PATENT AND TRADEMARK OFFICE
CERTIFICATE OF CORRECTION

PATENT NO.        : 7,522,796 B2
APPLICATION NO. : 10/597216
DATED             : April 21, 2009
INVENTOR(S)       : Tamotsu Uchida It is certified that error appears in the above-identified patent and that said Letters Patent is hereby corrected as shown below:

The drawing sheet, consisting of Figs. 11, 12, should be deleted to be replaced with the drawing sheet, consisting of Figs. 11, 12, as shown on the attached pages.

Signed and Sealed this

Tenth Day of November, 2009

David J. Kappos
*Director of the United States Patent and Trademark Office*

FIG. 11

PRIOR ART

FIG. 12

PRIOR ART